United States Patent [19]

Brankiewicz et al.

[11] Patent Number: 4,539,203
[45] Date of Patent: Sep. 3, 1985

[54] CL-1577D AND CL-1577E ANTIBIOTIC/ANTITUMOR COMPOUNDS, THEIR PRODUCTION AND USE

[75] Inventors: Alex J. Brankiewicz, Southfield; Richard H. Bunge, Ann Arbor; James C. French, Ann Arbor; Gerard C. Hokanson, Ann Arbor; Timothy R. Hurley, Ann Arbor; John P. Schaumberg, Ypsilanti, all of Mich.

[73] Assignee: Warner-Lambert Company, Morris Plains, NJ

[21] Appl. No.: 670,240

[22] Filed: Nov. 13, 1984

[51] Int. Cl.$^3$ .................... A61K 35/74; C12P 1/06
[52] U.S. Cl. .................... 424/117; 435/169
[58] Field of Search .................... 424/117; 435/169

*Primary Examiner*—Jerome D. Goldberg
*Attorney, Agent, or Firm*—Jerry F. Janssen

[57] ABSTRACT

Compounds CL-1577D and CL-1577E are prepared by cultivation of a purified isolate of Actinomycete designated ATCC 39363 in a culture medium having assimilable sources of carbon and nitrogen. The compounds are effective antimicrobial agents and possess cytotoxic activity against L1210 murine leukemia cells and P388 murine leukemia cells.

8 Claims, 6 Drawing Figures

CL-1577D AND CL-1577E ANTIBIOTIC/ANTITUMOR COMPOUNDS, THEIR PRODUCTION AND USE

CROSS-REFERENCE TO RELATED APPLICATIONS

This application discloses and claims subject matter related to subject matter contained in copending applications Ser. Nos. 512,088 and 665,894 both assigned to the assignee of the present invention.

BACKGROUND OF THE INVENTION

The present invention relates to novel antibiotic compounds which also demonstrate activity against transplanted tumors, and to a method of preparing such compounds by aerobic fermentation.

SUMMARY OF THE INVENTION

In accordance with one aspect of the present invention, there are provided the antibiotic compounds CL-1577D and CL-1577E, which compounds demonstrate both antimicrobial properties and activity against transplanted tumors.

In accordance with another aspect of the present invention, there are provided pharmaceutical compositions for treating microbial infections in a mammal comprising an antimicrobially effective amount of a material selected from the group consisting of CL-1577D, CL-1577E, and mixtures thereof, in combination with a pharmaceutically acceptable carrier.

In another aspect of the present invention, there is provided a method of treating microbial infections in a mammal comprising administering to a mammal in need of such treatment a pharmaceutical composition comprising an antimicrobially effective amount of a material selected from the group consisting of CL-1577D, CL-1577E, and mixtures thereof, in combination with a pharmaceutically acceptable carrier.

In yet another aspect of the present invention, there is provided a method of combatting tumors in a mammal comprising administering to a mammal in need of such treatment a pharmaceutical composition comprising a cytotoxically effective amount of a material selected from the group consisting of CL-1577D, CL-1577E, and mixtures thereof, in combination with a pharmaceutically acceptable carrier.

In a further aspect of the present invention, there is provided a method of preparing the compounds CL-1577D and CL-1577E by cultivating a purified isolate of Antinomycete designated ATCC 39363 under aerobic conditions in a medium containing assimilable sources of carbon and nitrogen until a substantial quantity of CL-1577D and CL-1577E is produced, and subsequently isolating one or both of the compounds.

DETAILED DESCRIPTION

In accordance with the present invention, anti-biotic compounds CL-1577D and CL-1577E are produced by cultivating a selected isolate of Actinomycete, ATCC 39363, under artificial conditions until a substantial quantity of the compounds are formed, and subsequently isolating one or more of the compounds.

The Actinomycete isolate suitable for the purpose of this invention was found in a soil sample collected in Tennessee, USA. This microorganism was isolated from the soil sample using a suitable agar plating medium, one containing salts such as potassium phosphate, potassium chloride, magnesium sulfate, and ferrous sulfate, and carbon sources such as glycerol and asparagine. To isolate the microorganism, the soil sample is pretreated with calcium carbonate before being plated onto the agar medium and, once plated, is incubated at a favorable temperature, particularly 33° C., to allow for the development of the soil microorganisms.

The CL-1577 complex producing organism that was isolated from the soil sample by the agar plating technique is an unidentified Actinomycete and has been deposited with the American Type Culture Collection, Rockville, Md. 20852, where it is being maintained in their permanent culture collection as ATCC 39363. This organism, designated as culture WP-444, which produces CL-1577D and CL-1577E and their congeners, is also being maintained as a dormant culture in lyophile tubes, cryogenic vials, and in soil tubes in the Warner-Lambert/Parke-Davis Culture Collection, 2800 Plymouth Road, Ann Arbor, Mich. 48105.

The microorganism designated ATCC 39363 was observed to have warty cell wall ornamentation and to have spore chain morphology characterized by short hooks.

Chromatographic analysis of digested cells indicated the presence of meso-2,6-diaminopimelic acid among the components of the cell walls, and the presence of madurose among the components of whole cell sugars. These compounds are indicative that the microorganism may belong to the genus Actinomadura.

The morphology and coloration of the microorgasim varies when grown on different culture media. Table 1 gives the color for the aerial mycelium, reverse color, substrate mycelium, and soluble pigment for the organism when grown on several culture media. The color code followed is that given in R. Eckerstrom and C. E. Foss (Eds.), *Color Harmony Manual,* 4th Ed., 1958, Container Corp. of America, Chicago, USA. Table 2 gives the physiological characteristics of the microorganism.

TABLE 1

| Culture Medium | Color |
| --- | --- |
| Coloration of Aerial Mycelium | |
| Yeast extract + malt extract agar (ISP-2) | No Spores |
| Oatmeal agar (ISP-3) | White |
| Inorganic salts + starch agar (ISP-4) | White |
| Glycerine-asparagine agar (ISP-5) | Slight white |
| Reverse (Substratal) Coloration | |
| Yeast extract + malt extract agar (ISP-2) | Light yellow |
| Oatmeal agar (ISP-3) | Light yellow |
| Inorganic salts + starch agar (ISP-4) | Pink to light red |
| Glycerol-asparagine agar (ISP-5) | Pink Soluble |

TABLE 1-continued

| Culture Medium | Pigment |
| --- | --- |
| Soluble Pigmentation | |
| Yeast extract + malt extract agar (ISP-2) | None |
| Oatmeal agar (ISP-3) | None |
| Inorganic salts + starch agar (ISP-4) | None |
| Glycerine-asparagine agar (ISP-5) | None |

TABLE 2

| Property | Characteristic |
| --- | --- |
| Melanin production | Negative |
| Nitrate reduction | Positive |
| Carbon source utilization | |
| D-Glucose | Positive |
| D-Xylose | Positive |
| L-Arabinose | Positive |
| L-Rhamnose | Positive |
| D-Fructose | Positive |
| D-Galactose | Positive |
| Raffinose | Positive |
| D-Mannitol | Positive |
| Inositol | Positive |
| Salicin | Negative |
| Sucrose | Positive |

The compounds CL-1577D and CL-1577E which demonstrate both antibiotic and antitumor properties, are produced by isolate ATCC 39363 during aerobic fermentation under controlled conditions. The fermentation medium consists of sources of carbon, nitrogen, minerals, and growth factors. Examples of carbon sources are glycerol and various simple sugars, such as glucose, mannose, fructose, xylose, ribose, or other carbohydrate-containing compounds such as dextrin, starch, cornmeal, and whey. The normal quantity of carbon source materials in the fermentation medium varies from about 0.1 to about 10 weight percent.

Nitrogen sources in the fermentation medium are organic, inorganic, or mixed organic-inorganic material. Examples of such materials are cottonseed meal, soybean meal, corn germ flour, corn steep liquor, distillers dried solubles, peanut meal, peptonized milk, and various ammonium salts.

The addition of minerals and growth factors are also helpful in the production of the CL-1577 complex of compounds. Examples of fermentation medium mineral additives include potassium chloride, sodium chloride, ferrous sulfate, calcium carbonate, cobaltous chloride, and zinc sulfate. Sources of growth factors include various yeast and milk products.

The preferred method of producing the CL-1577 complex of compounds is by submerged culture fermentation. According to this embodiment of the invention, the fermentation ingredients are prepared in solution or suspension and the mixture subsequently sterilized by autoclaving or steam heating. The pH of the aqueous medium is adjusted to preferably between about pH and about pH 8 and the mixture cooled following sterilization to a temperature between about 16° C. to about 45° C. The cooled, sterile fermentation medium is inoculated with the organism and thereafter fermentation is carried out with aeration and agitation.

In the submerged culture method, fermentation is carried out in shake-flasks or in stationary tank fermentors. In shake-flasks, aeration is achieved by agitation of the flasks to bring about mixing of the medium with air. In stationary tank fermentors, agitation is provided by impellers which may take the form of disc turbines, vaned discs, open turbine or marine propellers. Aeration is accomplished by injecting air or oxygen into the agitated mixture.

Adequate production of the CL-1577 complex of compounds is normally achieved under these conditions after a period of about two to ten days.

In an alternative embodiment, the CL-1577 complex of compounds may also be produced by solid state fermentation of the microorganism.

The following examples are provided to enable one skilled in the art to practice the present invention and are merely illustrative thereof. They are not to be viewed as limiting the scope of the invention as defined by the appended claims.

FERMENTATIVE PRODUCTION OF CL-1577 COMPLEX

EXAMPLE 1

The culture of *Actinomycete (ATCC* 39363) of the present invention, following its isolation from the agar plate, was transferred to an agar slant employing CIM 23 medium and incubated at 28° C. for 7 to 14 days.

TABLE 3

| Formulation of CIM 23 Medium | |
| --- | --- |
| Amidex corn starch | 1.0% |
| N-Z amine, type A | 0.2% |
| Beef Extract (Difco) | 0.1% |
| Yeast Extract (Difco) | 0.1% |
| Cobalt chloride pentahydrate | 0.002% |
| Agar | 2.0% |

EXAMPLE 2

A portion of the microbial growth from the agar slant was used to inoculate an 18-mm ×150-mm seed tube containing 5 ml of ARM 1550 seed medium. The inoculated seed was shaken at 33° C. for three days.

TABLE 4

| Formulation of ARM 1550 Seed Medium | |
| --- | --- |
| Bacto-Yeast extract (Difco) | 0.5% |
| Glucose monohydrate | 0.1% |
| Soluble starch (Difco) | 2.4% |
| Bacto-tryptone (Difco) | 0.5% |
| Bacto-Beef extract (Difco) | 0.3% |
| Calcium carbonate | 0.2% |

Note:
pH is adjusted to 7.5 with NaOH prior to adding the calcium carbonate.

EXAMPLE 3

A 1 ml portion of the microbial growth from the seed tube was transferred to a 300-ml baffled shake-flask containing 50 ml of SM-13 production medium.

TABLE 5

| Formulation of SM-13 Production Medium | |
| --- | --- |
| Dextrin-Amidex B411 (American Maize) | 1.5% |
| Lactose (Mallinckrodt) | 1.0% |
| Pharmamedia (Traders) | 0.65% |
| Fish meal (Zapata Haynie) | 0.35% |
| Torula yeast (St. Regis) | 0.25% |

The inoculated flask contents were incubated at 33° C. for four days with shaking (170 rpm gyratory shaker, 5 cm throw.) After a five day period, the fermentation beer was tan in color, the mycelia was granular in appearance, and the pH of the beer was about 6.4.

The antitumor activity of this fermentation broth was assayed at a dilution of 1:100 versus L1210 mouse leukemia cells grown in tissue culture. The assay technique is fully described in *Cancer Chemotherapy Reports,* Part 3, vol. 3, No. 2 (1972), Deran, Greenberg, MacDonald, Schumacher and Abbott. A broth which gave L1210 leukemia cell growth rates of 0 to 35%, compared with the growth of these cells under control conditions, was considered active, 0%, most active. The observed activities of the fermentation broth of Example 3 are given in Table 6.

TABLE 6

Antitumor Activity of Fermentation Broth from Example 3 (As Measured Against L1210 Mouse Leukemia Cells)

| Flask Number | % L1210 Cell Growth | |
| --- | --- | --- |
| | Supernate | Freeze-Dried Ethanol Extract |
| I | — | 8 |
| II | 10 | 31 |

The crude fermentation broth was also tested for antibacterial activity against various organisms using the agar-disc method. The crude broth was found to be active against *Alcaligenes viscolactis, Bacillus subtilis, Micrococcus luteus, Branhamella catarrhalis,* and *Staphylococcus aureus.*

EXAMPLE 4

A cryogenic vial containing approximately 1 ml of a suspension of the culture was used to inoculate 600 ml of SD-05 seed medium contained in a 2-liter baffled shake-flask. The inoculated flask contents were incubated for 76 hours at 33° C. on a gyratory shaker at 130 rpm.

TABLE 7

| Formulation of SD-05 Seed Medium | |
| --- | --- |
| Amberex 1003 (Amber Laboratories) | 0.5% |
| Glucose monohydrate (Cerelose, Corn Products) | 0.1% |
| Dextrin-Amidex B 411 (American Maize) | 2.4% |
| N-Z Case (Humko Sheffield) | 0.5% |
| Spray-dried meat solubles (Daylin Labs) | 0.3% |
| Calcium carbonate | 0.2% |
| Calcium carbonate | 0.2% |

After 76 hours, the contents of the seed flask were transferred aseptically to a 30-liter stainless steel fermentator containing 16 liters of SD-05 seed medium. The inoculated fermentor contents were incubated at 33° C. for 24 hours while being stirred at 300 rpm and sparged with air at a rate of 1 vol/vol/min.

EXAMPLE 5

The microbial growth from Example 4 was used to inoculate 75 gallons (284 liters) of SD-05 seed medium contained in a 200-gallon (757-liter) stainless steel fermentor. The medium was sterilized by steam heating at 121° C. for 40 minutes. The fermentor and contents were cooled to 33° C. and then inoculated with about 16 liters of the broth from Example 4. The resulting mixture was incubated at 33° C. for about 20 hours with stirring at 155 rpm, and sparged with air at a rate of 0.75 vol/vol/min.

EXAMPLE 6

The microbial growth from Example 5 was used to inoculate about 1300 gallons (4921 liters) of SM-121 medium contained in a 2000 gallon (7571 liter) stainless steel fermentor. The medium was sterilized prior to inoculation by heating with steam for 40 minutes at 121° C. After sterilization, the fermentor and contents were cooled to 33° C., inoculated, and incubated for five days with stirring at 125 rpm and air sparging at a rate of 0.75 vol/vol/min.

The SM-121 medium consisted of 1.75% by weight of a feed grade mixture composed of soybean meal, ground yellow corn, ground wheat, corn gluten meal, wheat middlings, dried milk products, animal fat preserved with BHA, ground beet pulp, calcium carbonate, sucrose, dehydrated alfalfa meal, dicalcium phosphate, brewers' dried yeast, salt, vitamin $B_{12}$ supplement, riboflavin supplement, calcium pantothenate, niacin, choline chloride, menadione sodium bisulfite (source of vitamin K activity), folic acid, pyridoxine hydrochloride, thiamin, ascorbic acid, vitamin A supplement, D activated animal sterol (source of vitamin $D_3$), vitamin E supplement, iron carbonate, iron sulfate, calcium iodate, manganous oxide, copper oxide, cobalt carbonate, zinc oxide.

The production of CL-1577 complex was monitored throughout the fermentation cycle by in vitro assay against L1210 mouse leukemia cells and by antimicrobial activity against *Micrococcus luteus.* In addition, such fermentation parameters as pH and percent sedimentation were recorded throughout the fermentation cycle. The data are presented in Table 8.

TABLE 8

| | | | | Observed Bioactivity | | | | | |
| --- | --- | --- | --- | --- | --- | --- | --- | --- | --- |
| Fermentation Time (Hours) | pH | Percent Sedimentation (Growth) | Inhibition of Growth of *Micrococcus luteus* Inhibition Zone Dia. (mm) | Percent Growth of L1210 Mouse Leukemia Cells at Given Dilution | | | | | |
| | | | | 1:500 | 1:2500 | 1:5000 | 1:10,000 | 1:30,000 | 1:100,000 |
| 0 | 6.65 | 0 | 0 | NA* | — | NA* | — | — | — |
| 24 | 8.10 | 10.0 | 0 | NA* | — | NA* | — | — | — |
| 46 | 7.40 | 29.3 | 17 | 5.1 | — | 13.9 | — | — | — |
| 75 | 7.30 | 25.4 | 21 | — | 2.3 | — | 7.6 | 15.7 | 29.2 |
| 96 | 7.90 | 20.0 | 22 | — | 2.8 | — | 5.8 | 12.1 | 17.1 |
| 116 | 8.20 | 25.4 | 22.5 | — | 1.6 | — | 4.7 | 11.2 | 30.4 |

*NA = Not active.

After 116 hours of fermentation, the 1140 gallons (4315 liters) of fermentation beer was harvested and the CL-1577 complex of compounds isolated as described below.

ISOLATION OF CL-1577D and CL-1577E

Fermentation beer (4500 liters), produced from *Actinomycete* culture ATCC 39363 in the manner described above was stirred for one hour with 3200 liters of ethyl acetate. Celite 545 (115 kg) was then added and the mixture filtered using a 79 cm plate and frame filter press. The filter cake was washed twice with 280-liter portions of ethyl acetate and the washes were added to the filtrate. The lower aqueous layer was separated and the organic extract was concentrated in vacuo to 29.5 liters. This concentrate was diluted with 91 liters petroleum ether and the mixture was extracted with 22 liters of methanol-H₂O (1:1). The lower aqueous methanol layer (25 liters) was extracted with 7 liters of petroleum ether and then concentrated to 3 liters. All of the organic-soluble material that remained was carefully transferred to 9 liters of ethyl acetate. This solution was dried (Na₂SO₄) and concentrated to 2 liters. The concentrate was diluted with 4 liters of CH₂Cl₂ and stored overnight at −20° c. Insoluble material was removed by filtration using 200 g of Celite 545. After filtration the Celite pad was washed with 1 liter of CH₂Cl₂-ethyl acetate (2:1). The washes and filtrate were combined (7 liters) and diluted with 1.5 liters CH₂Cl₂. This solution was added to a 10 cm (i.d.) column containing 8.2 kg of 40 μm aminopropyl-silica gel (Analytichem International, Inc., Harbor City, Calif. packed in CH₂Cl₂. The resin was then eluted sequentially with 44 liters of CH₂Cl₂; 30 liters of CHCl₃-CH₂Cl₂ (65:35); 50 liters of CHCl₃-CH₂Cl₂ (70:30); 30 liters of CHCl₃-CH₂Cl₂ (80:20) and 30 liters of CHCl₃-ethanol (95:5). After a hold-up volume of approximately 4 liters was collected, the fractions listed in Table 9 were collected.

TABLE 9

Fractionation of a Crude Complex of CL-1577 Components Over Aminopropyl Silica Gel

| Fraction Number | Volume (Liters) | Fraction Number | Volume (Liters) |
|---|---|---|---|
| 1 | 12 | 13 | 8 |
| 2 | 16 | 14 | 8 |
| 3 | 16 | 15 | 5 |
| 4 | 12 | 16 | 8 |
| 5 | 6 | 17 | 8 |
| 6 | 2 | 18 | 8 |
| 7 | 2 | 19 | 8 |
| 8 | 2 | 20 | 16 |
| 9 | 2 | 21 | 11 |
| 10 | 2 | 22 | 8.5 |
| 11 | 4 | 23 | 8 |
| 12 | 4 | 24 | 8 |

Fractions 21 and 22 were combined and concentrated in vacuo to 150 ml. This concentrate was mixed with petroleum ether (1.2 liters) to precipitate 4.15 g of a solid (Product A) that contained approximately 350 mg of CL-1577D and 440 mg of CL-1577E.

A 7 cm (i.d.)×88 cm stainless steel column was dry-packed with 1.9 kg of 40 μm C₁₈-silica gel (Analytichem International, Inc, Harbor City, Calif.). After the adsorbent was washed with 10 liters of methanol followed by 10 liters of 0.05 M ammonium acetate pH 6.8 buffer-methanol (25:75), a portion (3.5 g) of Product A in 30 ml of 90% MeOH was applied to the top of the column and chromatographed using 0.05 M ammonium acetate pH 6.8 buffer-methanol (25:75) as the mobile phase. The fractions listed in Table 10 were collected.

TABLE 10

Chromatography of Product A Over C₁₈—Silica Gel

| Fraction Number | Volume (Liters) | Fraction Number | Volume (Liters) |
|---|---|---|---|
| 1 | 3.5 | 8 | 0.7 |
| 2 | 2.0 | 9 | 2.0 |
| 3 | 2.0 | 10 | 2.0 |
| 4 | 2.0 | 11 | 2.0 |
| 5 | 1.1 | 12 | 2.0 |
| 6 | 2.0 | 13 | 2.0 |
| 7 | 0.8 | 14 | 7.5 |

Fractions 4, 5, and 6 were combined and concentrated in vacuo to 1.3 liters. This concentrate was extracted twice with 400 ml portions of CHCl₃. The CHCl₃ extracts were combined, washed with 200 ml of H₂O, dried over Na₂SO₄, and concentrated to 5 ml. Addition of 35 ml of cyclohexane to this concentrate precipitated 325 mg of a solid (Product B) which contained approximately 250 mg of CL-1577D.

Fractions 8, 10, 11, 12, and 13 were combined and concentrated in vacuo to 1.3 liters. This concentrate was extracted twice with 400 ml portions of CHCl₃. The CHCl₃ extracts were combined, washed with 200 ml of water, dried over Na₂SO₄, and concentrated to 5 ml. This concentrate was mixed with 35 ml of cyclohexane to precipitate 342 mg of a solid (Product C) which contained approximately 200 mg of CL-1577E.

PURIFICATION AND PROPERTIES OF CL-1577D

A 103 mg portion of semipurified CL-1577D (Product B) was dissolved in 1 ml of methanol and chromatographed over 60 g of C-18 silca gel (40 μm particle size, Analytichem International, Harbor City, Calif.) packed in a 25 mm (i.d.)×300 mm glass column. The silica gel was prepared for chromatography by washing with methanol and then equilibrating with a mobile phase consisting of 0.1 M sodium acetate pH 4.0 buffer-methanol-acetonitrile (40:30:30), adjusted to pH 4.6–4.8 with acetic acid. After application of the charge, the column was eluted with the same buffer-methanol-acetonitrile solvent system. Several factions were collected and each was assayed by high pressure liquid chromatography using the system described in the following section. Fractions containing the bulk of CL-1577D were combined. The combined eluates (350 ml) were extracted once with a mixture of dichloromethane (350 ml) and 10% aqueous sodium chloride (350 ml). The organic layer was removed and the aqueous layer extracted once more with dichloromethane (350 ml). The organic extracts were combined, washed with water (350 ml), and reduced to dryness to give 46 mg of purified Cl-1577D.

The purified CL-1577D was further processed using semipreparative high pressure liquid chromatography over C-18 silica gel (Magnum 9 ODS-3, Whatman Clinical Separation, Inc, Clifton, N.J., USA) using a 9.4 mm (i.d.)×25 cm column. The silica gel was prepared by washing with methanol and then equilibrating with a mobile phase consisting of 0.1 M sodium acetate pH 4.0 buffer-methanol-acetonitrile (45:30:25), adjusted to pH 4.6–4.8 with acetic acid. A 5 mg portion of the purified CL-1577D from above was dissolved in 0.1 ml of methanol and applied to the column. The column was eluted with the same buffer-methanol-acetonitrile system used for the pretreatment of the adsorbent. Several fractions were collected and those containing CL-1577D as the only UV absorbing peak were combined. This process was repeated with three other 5 mg portions and the fractions containing CL-1577D from each chromatographic run were combined. The combined eluates (90 ml) were extracted with a mixture of dichloromethane (90 ml) and 10% aqueous sodium chloride (90 ml). The organic layer was removed and the aqueous layer extracted with dichloromethane once again. The combined organic extracts were washed with water (90 ml) and reduced to dryness to give 6.2 mg of CL-1577D.

Figure 1:
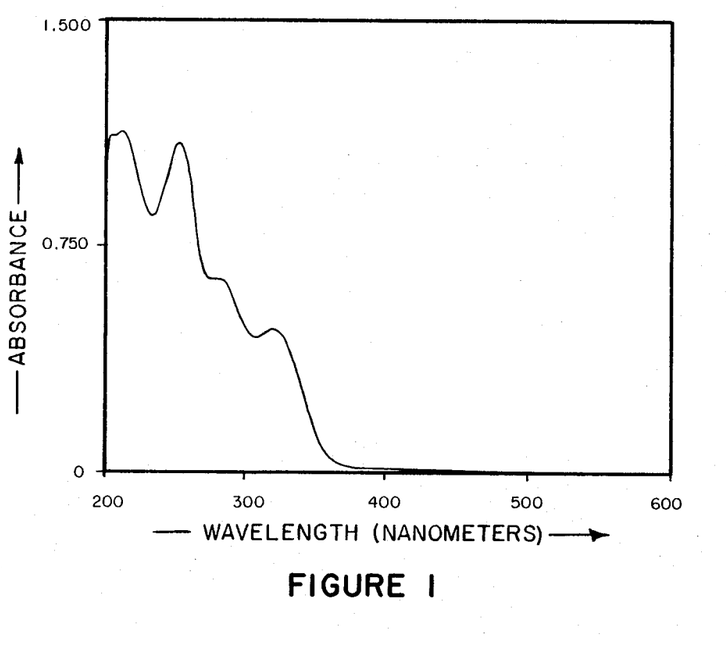
FIG. 1 is the ultraviolet spectrum of CL-1577D in methanol solution.
Figure 2:
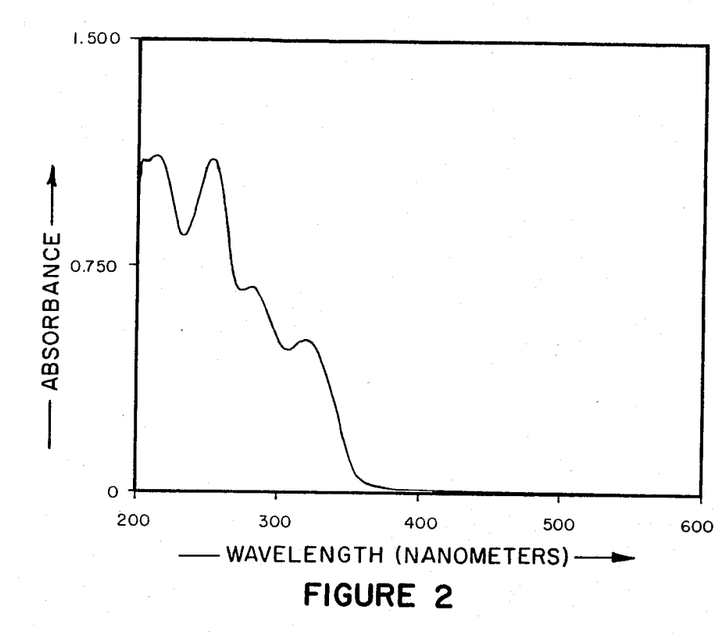
FIG. 2 is the ultraviolet spectrum of CL-1577E in methanol solution.
Figure 3:
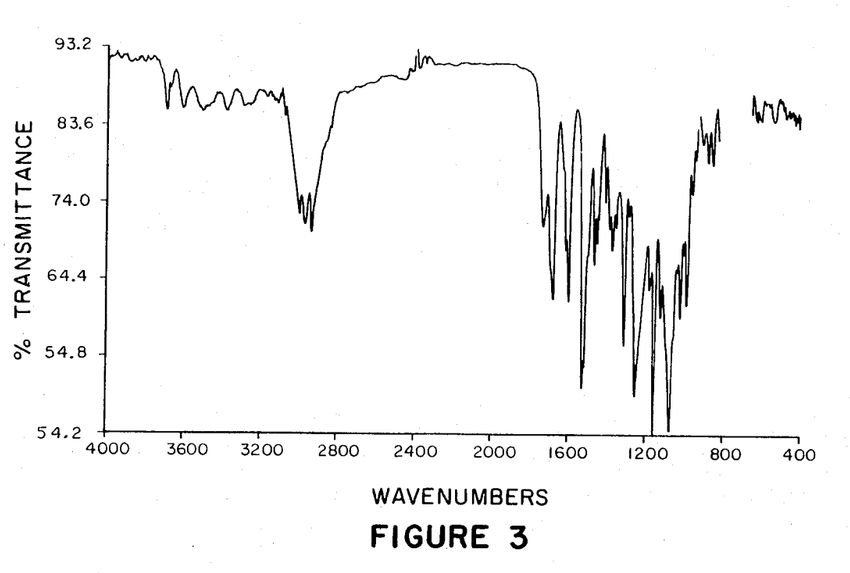
FIG. 3 is the infrared spectrum of CL-1577D in chloroform solution.

| Properties of CL-1577D | |
|---|---|
| Ultraviolet absorption in methanol (FIG. 1) | λ max   a<br>320    9.48<br>281   12.76<br>252   21.74<br>212   22.48 |
| Infrared absorption spectrum in chloroform (FIG. 2) | Principal absorption peaks at 2939, 1733, 1679, 1598, 1527, 1466, 1409, 1374, 1312, 1252, 1158, 1123, 1075, 1023, 989, and 963 reciprocal centimeters |
| 200 MHz proton magnetic resonance spectrum in deuterochloroform (FIG. 3) | Principal signals at 1.10 (d), 1.23–1.40 (m), 1.42–2.08 (m), 2.10 (s), 2.00–2.55 (m), 2.60–2.87 (m), 3.39 (s), 3.30–4.16 (m), 3.77 (s), 3.86 (s), 3.95 (s), 4.41–4.70 (m), 4.97 (d), 5.21 (m), 5.46 (m), 5.67–5.91 (m), 6.17 (s), 6.39 (m), 7.47 (s), 8.58 (s), and 11.70 (s) parts per million downfield from tetramethylsilane |
| Molecular weight and formula (by mass spectrometry) | 1402 atomic mass units $C_{55}H_{94}N_4O_{29}S_4$ |
| High pressure liquid chromatography | |
| Column: | Partisil 10 ODS-3 C-18 silica gel (Whatman Chemical Separation, Inc, Clifton, New Jersey, USA), 4.6 mm (i.d.) × 25 cm |
| Mobile phase: | 0.05 M Ammonium phosphate pH 7.1 buffer-acetonitrile (45:55) |
| Flow rate: | 2.0 ml/min |
| Detection: | Ultraviolet absorption at 254 nm |
| Retention time: | 6.5 min |
| Thin-layer chromatography | |
| Stationary Phase: | Silica gel 60 F-254 (Merck & Co, Rahway, New Jersey, USA) |
| Mobile phase: | Chloroform-methanol (92:8) |
| Rf: | 0.32 |

Figure 4:
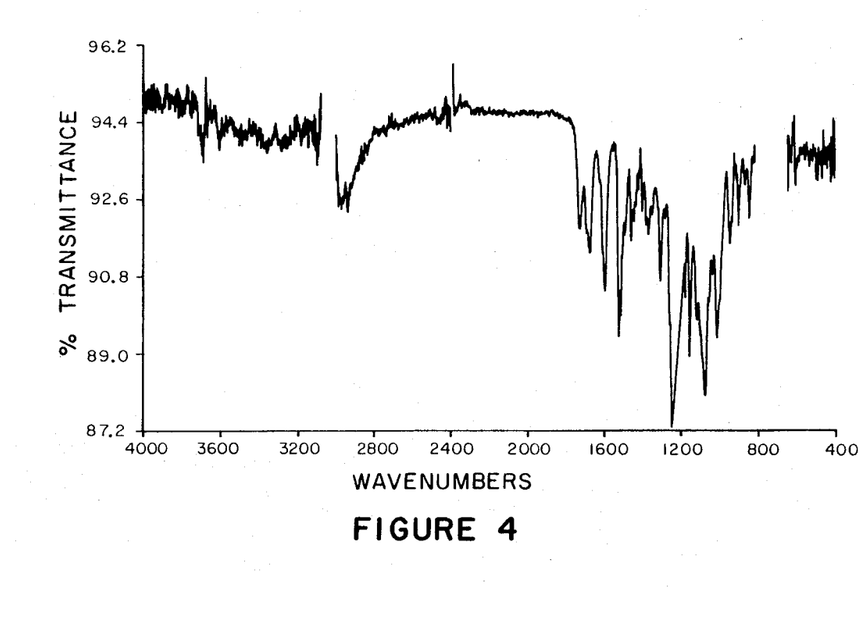
FIG. 4 is the infrared spectrum of CL-1577E in chloroform solution.
Figure 5:
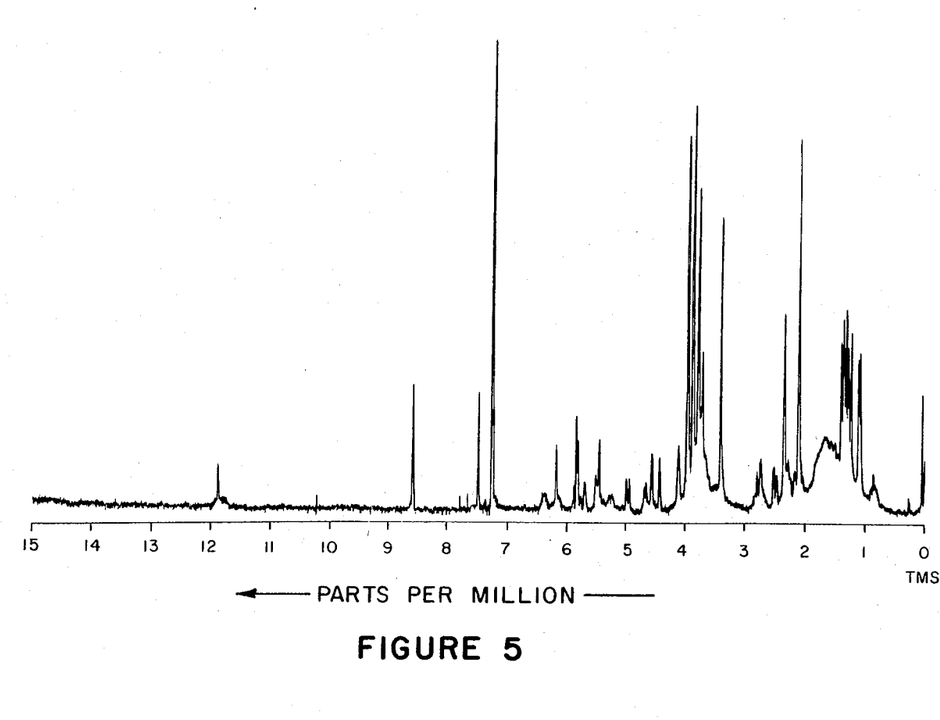
FIG. 5 is the 200 MHz proton magnetic resonance spectrum of CL-1577D in deuterochloroform solution.
Figure 6:
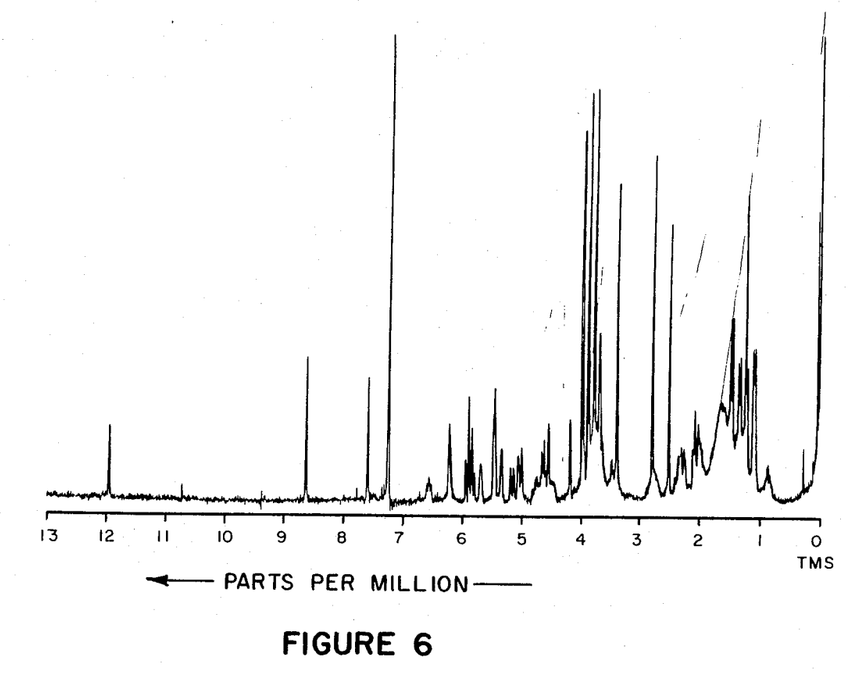
FIG. 6 is the 200 MHz proton magnetic resonance spectrum of CL-1577E in deuterochloroform solution.

| Properties of CI-1577E | |
|---|---|
| Ultraviolet absorption in methanol (FIG. 4) | λ max   a<br>320   10.04<br>282   13.58<br>253   22.08<br>213   22.30 |
| Infrared absorption spectrum in chloroform (FIG. 5) | Principal absorption peaks at 2939, 1734, 1679, 1601, 1527, 1466, 1410, 1376, 1312, 1249, 1181, 1158, 1121, 1078, 1040, 1017, and 954 reciprocal centimeters |
| 200 MHz proton magnetic resonance spectrum in deuterochloroform (FIG. 6) | Principal signals at 1.09 (d), 1.15–1.50 (m), 1.50–2.10 (m), 2.20–2.40 (m), 2.50 (s), 2.65–2.90 (m), 2.78 (s), 3.39 (s), 3.30–4.10 (m), 3.77 (s), 3.87 (s), 3.97 (s), 4.18 (s), 4.40–4.90 (m), 5.00–5.30 (m), 5.33–5.47 (m), 5.60–5.95 (m), 6.22 (s), 6.60 (m), 7.56 (s), 8.62 (s), and 11.93 (s) ppm downfield from tetramethylsilane |
| Molecular weight and formula (by mass spectrometry) | 1418 atomic mass units $C_{55}H_{94}N_4O_{30}S_4$ |
| High pressure liquid chromatography | |
| Column: | Partisil ODS-3 C-18 silica gel (Whatman Chemical Separation, Inc, Clifton, New Jersey, USA) 4.6 mm i.d. × 25 cm |
| Mobile phase: | 0.05 M Ammonium phosphate pH 7.1 buffer-acetonitrile (45:55) |
| Flow rate: | 2.0 ml/min |
| Detection: | Ultraviolet absorption at 254 nm |
| Retention time: | 6.8 min |
| Thin-layer chromatography | |
| Stationary phase: | Silica gel 60 F-254 (Merck & Co, Rahway, New Jersey, USA) |
| Mobile phase: | chloroform-methanol (92:8). |
| Rf: | 0.49 |

PURIFICATION AND PROPERTIES OF CL-1577E

CL-1577E was purified by semipreparative high pressure liquid chromatography using a C-18 silica gel column (Magnum 9 ODS-3, Whatman Chemical Separation Inc, Clifton, N.J. USA). A 7 mg portion of semipurified CL-1577E (Product C from above) was dissolved in 0.1 ml of methanol and applied to the above-described column (previously washed with methanol and equilibrated with the buffered mobile phase). Elution with 0.1 M sodium acetate pH 4.0 buffer—methanol-acetonitrile (45:35:25), adjusted to pH 4.6–4.8 with acetic acid, afforded fractions containing CL-1577E as the only UV-absorbing component as determined by high pressure liquid chromatographic assay. These fractions and the corresponding fractions from two identical chromatographic runs were combined (90 ml), mixed with 10% aqueous sodium chloride (90 ml), and extracted with dichloromethane (90 ml). The organic layer was removed and the aqueous layer extracted again with dichloromethane (90 ml). The organic extracts were combined, washed with water (90 ml), and dried to give 5.6 mg of CL-1577E.

BIOLOGICAL ACTIVITY OF CL-1577D AND CL-1577E

The biological activity of the compounds of this invention against five species of gram-negative bacteria, seven species of gram-positive bacteria, four species of yeast, and two species of fungi was determined using the microtiter dilution technique. This method is described by T. B. Conrath, "Handbook of Microtiter Procedures," Dynatech Corp., Cambridge, Mass., USA (1972); and T. L. Gavan nd A. L. Barry, "Microdilution Test Procedures" in *Manual of Clinical Microbiology*, E. H. Lennett ed., American Soc. for Microbiol., Washington D.C., USA (1980).

Each agent is dissolved in a nonaqueous solvent for several minutes to sterilize the compound or, if the compound is completely soluble in water, the aqueous solution is sterilized by passage through a 0.2 to 0.45 micron membrane filter.

Each well of a sterile 96-well microdilution tray is filled under aseptic conditions with 0.1 ml of Meuller-Hinton broth for antibacterial tests, and yeast extract-peptone-dextrose or buffered, supplemented yeast nitrogen base for tests using yeasts or fungi.

A 0.5 ml sample of the test compound solutions is added to each of the eight wells in the first row. A microdilutor apparatus is used to simultaneously mix the contents of these wells and to transfer aliquots to each succeeding row of cells to obtain a range of serially diluted solutions, e.g., concentrations of 1000, 333, 111, 37, 12.3, 4.1, 1.37, and 0.46 micrograms/ml. The last row of wells is untreated and serves as a control.

Each well containing broth and test compound is inoculated with about ten microliters of inoculum of the test microorganism. One well in the last row of wells (which are free of test compound) is not inoculated to provide a sterility control. The trays are sealed and incubated. Media inoculated with bacteria are incubated at 37° C. for 16–24 hours, while those containing yeasts or fungi are incubated at 28° C. for 36–48 hours. During incubation, the inoculated medium is shaken at 100–140 rpm to increase contact between the cells and test compounds.

After the incubation period, each plate is placed on a test reading mirror and the inhibition end points are observed and recorded. The lowest concentration of test compound producing inhibition of the growth of the microorganism (MIC value) is used as the measure of the activity of the test compound. MIC values of <0.5 µg/ml to 333 µg/ml are considered indicative of activity; MIC values of 333 µg/ml to 1000 µg/ml are considered indicative of marginal activity; and MIC values of 221000 µg/ml are considered indicative of inactivity of the test compound against the given microorganism.

The antimicrobial activities of CL-1577D and CL-1577E appear in Tables 11 and 12, respectively.

TABLE 11

Antimicrobial Activity of CL-1577D

| Microorganism | Minimal Inhibitory Concentration (ng/ml) |
|---|---|
| Escherichia coli | 111 |
| Salmonella typhimurium | 37 |
| Alcaligenes viscolactis | <0.46 |
| Branhamella catarrhalis | <0.46 |
| Pseudomonas aeruginosa | 111 |
| Micrococcus luteus | <0.46 |
| Staphylococcus aureus | <0.46 |
| Streptococcus pyogenes | <0.46 |
| Streptococcus pneumoniae | <0.46 |
| Streptococcus faecalis | <0.46 |
| Bacillus cereus | <0.46 |
| Bacillus megaterium | <0.46 |
| Saccharomyces cerevisiae | 111 |
| Schizosaccharomyces pombe | <0.46 |
| Rhodotorula aurantiaca | <0.46 |
| Torulopsis albida | 111 |
| Mucor paraciticus | 333 |
| Rhizopus japonicus | 333 |

TABLE 12

Antimicrobial Activity of CL-1577E

| Microorganism | Minimal Inhibitory Concentration (ng/ml) |
|---|---|
| Escherichia coli | 111 |
| Salmonella typhimurium | 37 |
| Alcaligenes viscolactis | <0.46 |
| Branhamella catarrhalis | <0.46 |
| Pseudomonas aeruginosa | 111 |
| Micrococcus luteus | <0.46 |
| Staphylococcus aureus | <0.46 |
| Streptococcus pyogenes | <0.46 |
| Streptococcus pneumoniae | <0.46 |

TABLE 12-continued

Antimicrobial Activity of CL-1577E

| Microorganism | Minimal Inhibitory Concentration (ng/ml) |
|---|---|
| Streptococcus faecalis | <0.46 |
| Bacillus cereus | <0.46 |
| Bacillus megaterium | <0.46 |
| Saccharomyces cerevisiae | 37 |
| Schizosaccharomyces pombe | <0.46 |
| Rhodotorula aurantiaca | 1.4 |
| Torulopsis albida | 111 |
| Mucor paraciticus | 333 |
| Rhizopus japonicus | 1000 |

The data appearing in Tables 11 and 12 indicates that both CL-1577D and CL-1577E possess considerable activity as agents against a wide range of gram-negative and gram-positive bacteria and fungi.

CYTOTOXIC ACTIVITY OF CL-1577D and CL-1577E AGAINST L1210 MURINE LEUKEMIA CELLS IN VITRO The cytotoxic antitumor activity of CL-1577D and CL-1577E against L1210 murine leukemia cells in vitro were determined using the method detailed in R. I. Geran, et al., "Protocols for Screening Chemical Agents and Natural Products Against Animal Tumors and Other Biological System,"] 3rd Edition, *Cancer Chemotherapy Reports*, Part 3, Vol. 3, 1–87 (1972) which is incorporated herein by reference. From duplicate tests the cytotoxic activity was determined as shown in Table 13.

TABLE 13

Cytotoxic Activity of CL-1577D and CL-1577E Against L1210 Leukemia Cells

| Compound | $IC_{50}$ (ng/ml) |
|---|---|
| CL-1577D | 0.022 |
| CL-1577E | 0.077 |

The in vivo antitumor activities of CL-1577D and CL-1577E against P388 murine leukemia were determined in accordance with the protocol in Geran, et al cited above. The mice were infected intraperitoneally on Day 0 and then administered appropriate doses of CL-1577D or 1577E on Days 1–9. The results of these tests are listed in Table 14.

TABLE 14

In Vivo Activity of CL-1577D and CL-1577E Against P388 Leukemia in Mice

| Dosage (µg/kg/injection) | % T/C* For CL-1577D | % T/C* For CL-1577E |
|---|---|---|
| 50 | toxic | toxic |
| 25 | toxic | toxic |
| 12.5 | 105 | 137 |
| 6.25 | 214 | 137 |

*% T/C = $\dfrac{\text{Median survival time of treated mice}}{\text{Median survival time of control mice}} \times 100$ The compounds CL-1577D and CL-1577E can be used for their antimicrobial activity as well as for their antitumor activity in the form of pharmaceutical compositions in combination with suitable compatible pharmaceutically acceptable carriers. These compositions may also contain other antimicrobial and/or antitumor agents. The compositions are made-up in a pharmaceutically acceptable form appropriate for the desired route of administration. Examples of such forms include solid forms for oral administration as tablets, capsules, pills, powders and granules, liquid forms for topical or oral administration as solutions, emulsions, suspensions, syrups, and elixirs, and forms suitable for parenteral administration such as sterile solutions, suspensions, or emulsions.

For use as antimicrobial agents, the compositions are administered so that the concentration of the composition exceeds that required for the minimal inhibition of the particular microorganism sought to be controlled.

We claim:

1. Sulfur-containing antibiotic compounds CL-1577D or CL-1577E Compound CL-1577D having the molecular formula $C_{55}H_{94}N_4O_{29}S_4$ characterized by the following properties:
   (a) an ultraviolet absorption spectrum in methanol having absorption maxima at 320 (a=9.48), 281 (a=12.76), 252 (a=21.74), and 212 (a=22.48) nanometers;
   (b) an infrared absorption spectrum in chloroform having absorption peaks at 2939, 1733, 1679, 1598, 1527, 1466, 1409, 1374, 1312, 1252, 1158, 1123, 1075, 1023, 989, and 963 reciprocal centimeters; and
   (c) a 200 MHz nuclear magnetic resonance spectrum in deuterochloroform having principal signals at 1.10 (doublet), 1.23–1.40 (multiplet), 1.42–2.08 (multiplet), 2.10 (singlet), 2.00–2.55 (multiplet), 2.60–2.87 (multiplet), 3.39 (singlet), 3.30–4.16 (multiplet), 3.77 (singlet), 3.86 (singlet), 3.95 (singlet), 4.41–4.70 (multiplet), 4.97 (doublet), 5.21 (multiplet), 5.46 (multiplet), 5.67–5.91 (multiplet), 6.17 (singlet), 6.39 (multiplet), 7.47 (singlet), 8.58 (singlet), and 11.70 (singlet) parts per million downfield from tetramethylsilane;

Compound CL-1577E having the molecular formula $C_{55}H_{94}N_4O_{30}S_4$ characterized by the following properties
   (a) an ultraviolet absorption spectrum in methanol having absorption maxima at 320 (a=10.04), 282 (a=13.58), 253 (a=22.08), and 213 (a=22.30) nanometers;
   (b) an infrared absorption spectrum in chloroform having absorption peaks at 2939, 1734, 1679, 1601, 1527, 1466, 1410, 1376, 1312, 1249, 1181, 1158, 1121, 1078, 1040, 1017, and 954 reciprocal centimeters; and
   (c) a 200 MHz nuclear magnetic resonance spectrum in deuterochloroform having principal signals at 1.09 (doublet), 1.15–1.50 (multiplet), 1.50–2.10 (multiplet), 2.20–2.40 (multiplet), 2.50 (singlet), 2.65–2.90 (multiplet), 2.78 (singlet), 3.39 (singlet), 3.30–4.10 (multiplet), 3.77 (singlet), 3.87 (singlet), 3.97 (singlet), 4.18 (singlet), 4.40–4.90 (multiplet), 5.00–5.30 (multiplet), 5.33–5.47 (multiplet, 5.60–5.95 (multiplet), 6.22 (singlet), 6.60 (multiplet), 7.56 (singlet), 8.62 (singlet), and 11.93 (singlet) parts per million downfield from tetramethylsilane.

2. Compound CL-1577D as defined in claim 1.

3. Compound CL-1577E as defined in claim 1.

4. A method of preparing compounds CL-1577D or CL-1577E as defined in claim 1, which comprises cultivating a purified isolate of *Actinomycete* designated ATCC 39363 under aerobic conditions in a medium containing assimilable sources of carbon and nitrogen until a substantial quantity of the compounds are formed and thereafter isolating the compounds in a pure form.

5. A pharmaceutical composition for treating bacterial infections in a mammal comprising an antibacterially effective amount of compound CL-1577D as defined in claim 1 in combination with a pharmaceutically acceptable carrier.

6. A method of treating bacterial infections in a mammal which comprises administering to a mammal in need of such treatment an antibacterially effective amount of a pharmaceutical composition as defined by claim 5.

7. A pharmaceutical composition for treating bacterial infections in a mammal comprising an antibacterially effective amount of compound CL-1577E as defined in claim 1 in combination with a pharmaceutically acceptable carrier.

8. A method of treating bacterial infections in a mammal which comprises administering to a mammal in need of such treatment an antibacterially effective amount of a pharmaceutical composition as defined by claim 7.

* * * * *